(12) United States Patent
Majumder et al.

(10) Patent No.: US 9,394,215 B2
(45) Date of Patent: Jul. 19, 2016

(54) PROCESSES FOR MAKING $C_x$-$C_y$ OLEFINS FROM $C_5$ AND $C_6$ PARAFFINS

(75) Inventors: Debarshi Majumder, Forest Park, IL (US); Stephen Wayne Sohn, Arlington Heights, IL (US); Bryan K. Glover, Algonquin, IL (US); Andrea G. Bozzano, Northbrook, IL (US)

(73) Assignee: UOP LLC, Des Plaines, IL (US)

( * ) Notice: Subject to any disclaimer, the term of this patent is extended or adjusted under 35 U.S.C. 154(b) by 342 days.

(21) Appl. No.: 13/186,205

(22) Filed: Jul. 19, 2011

(65) Prior Publication Data

US 2013/0023708 A1   Jan. 24, 2013

(51) Int. Cl.

| | |
|---|---|
| *C07C 2/64* | (2006.01) |
| *C07C 2/04* | (2006.01) |
| *C07C 2/54* | (2006.01) |
| *C07C 2/56* | (2006.01) |
| *C07C 2/72* | (2006.01) |
| *C07C 6/04* | (2006.01) |
| *C07C 303/06* | (2006.01) |
| *C07C 2/06* | (2006.01) |
| *C07C 5/32* | (2006.01) |

(Continued)

(52) U.S. Cl.
CPC ... *C07C 6/04* (2013.01); *C07C 2/06* (2013.01); *C07C 2/64* (2013.01); *C07C 5/32* (2013.01); *C07C 303/06* (2013.01); *C10G 50/00* (2013.01); *C10G 69/126* (2013.01)

(58) Field of Classification Search
USPC ......... 585/328, 329, 330, 518, 323, 510–516; 208/133, 134, 141, 41; 562/94
See application file for complete search history.

(56) References Cited

U.S. PATENT DOCUMENTS

| | | | | |
|---|---|---|---|---|
| 2,143,566 | A |   | 1/1939 | Moser |
| 3,485,881 | A | * | 12/1969 | Zuech ............................. 585/513 |
| 3,658,927 | A | * | 4/1972 | Crain et al. .................... 585/367 |

(Continued)

FOREIGN PATENT DOCUMENTS

WO   2011045533 A1   4/2011

OTHER PUBLICATIONS

International Search Report and Written Opinion dated Feb. 22, 2013 for PCT/US2012/041193, Applicant's file reference H0029765.

(Continued)

*Primary Examiner* — In Suk Bullock
*Assistant Examiner* — Youngsul Jeong

(57) ABSTRACT

Processes for making $C_X$ to $C_Y$ olefins are provided. The processes include reacting a feedstock comprising $C_5$ and $C_6$ olefins under dimerization or oligomerization conditions to provide a dimerization or oligomerization product. The product is separated into a stream comprising unreacted $C_5$ and $C_6$ paraffins, a stream comprising $C_{10}$ to $C_{X-1}$ olefins, and a stream comprising $C_X$ to $C_Y$ olefins, wherein X is at least 14 and Y is greater than X and less than or equal to 36.

19 Claims, 1 Drawing Sheet

(51) Int. Cl.
*C10G 50/00* (2006.01)
*C10G 69/12* (2006.01)

(56) References Cited

U.S. PATENT DOCUMENTS

| | | | |
|---|---|---|---|
| 4,317,948 A * | 3/1982 | Heckelsberg | 585/329 |
| 4,450,311 A | 5/1984 | Wright | |
| 4,895,997 A | 1/1990 | Hamilton, Jr. et al. | |
| 5,073,351 A | 12/1991 | Beech | |
| 5,196,625 A | 3/1993 | Threlkel | |
| 5,780,694 A | 7/1998 | Singleton | |
| 5,811,608 A | 9/1998 | Stine | |
| 6,222,077 B1 | 4/2001 | Singleton | |
| 7,572,947 B2 | 8/2009 | Brown et al. | |
| 7,683,226 B1 | 3/2010 | Glover et al. | |
| 7,781,630 B2 | 8/2010 | Glover et al. | |
| 7,781,631 B2 | 8/2010 | Glover et al. | |
| 7,781,632 B2 | 8/2010 | Glover et al. | |
| 2005/0016899 A1 | 1/2005 | Abazajian | |
| 2007/0015945 A1 | 1/2007 | Louret | |
| 2007/0021317 A1 * | 1/2007 | Le Coent et al. | 510/424 |
| 2007/0191662 A1 * | 8/2007 | Oikarinen et al. | 585/533 |
| 2009/0292150 A1 * | 11/2009 | Glover et al. | 585/316 |
| 2010/0004496 A1 | 1/2010 | Glover et al. | |

OTHER PUBLICATIONS

European search report for 128142601-361 /2739591 PCT/US2012041193, dated Feb. 24, 2015, Reference: MDP/P130793EP00; Applicant's file reference H0029765.

* cited by examiner

PROCESSES FOR MAKING $C_X$-$C_Y$ OLEFINS FROM $C_5$ AND $C_6$ PARAFFINS

FIELD OF THE INVENTION

The present invention generally relates to processes for making heavy olefins, and more particularly relates to processes for making $C_X$ to $C_Y$ olefins from $C_5$ and $C_6$ paraffins.

BACKGROUND OF THE INVENTION

High molecular weight olefins, or "heavy olefins," particularly olefins having carbon chains with 14 to 36 carbons, particularly 18 to 28 carbons, have found many utilities, especially in the production of surfactants for specialty applications. (As used herein, molecules with carbon chains having X carbons will be designated $C_X$. Molecules with carbon chains have more than X carbons will be designate $C_{X+}$.) The most significant growth in demand is expected in the area of enhanced oil-recovery processes, driven by an always continuing increase in crude prices. $C_{18}$ to $C_{28}$ olefins are especially desirable in the production of alkylbenzene surfactants and sulfonated surfactants used in tertiary oil-recovery processes.

Typically, heavy olefins are obtained from heavy feedstock, that is, feedstock having heavy olefins and high molecular weight paraffins ("heavy paraffins"). The heavy olefins are obtained by separating them from the heavy paraffins. However, it is very difficult and, thus, costly to extract the heavy olefins from the heavy paraffins. In addition, the heavy feedstock has a high fuel value in itself. In contrast, feedstocks comprising lower molecular weight ($C_5$ and $C_6$) paraffins are relatively inexpensive.

Accordingly, it is desirable to provide a method for making heavy olefins from feedstock comprising lower molecular weight ($C_5$ and $C_6$) paraffins. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

Processes for making $C_X$ to $C_Y$ olefins are provided. In accordance with one embodiment, a process includes reacting a feedstock comprising $C_5$ and $C_6$ olefins under dimerization or oligomerization conditions to provide a dimerization or oligomerization product. The dimerization or oligomerization product is separated into a stream comprising unreacted $C_5$ and $C_6$ paraffins, a stream comprising $C_{10}$ to $C_{X-1}$ olefins, and a stream comprising $C_X$ to $C_Y$ olefins, wherein X is at least 14 and Y is greater than X and less than or equal to 36.

In another embodiment, a process for making $C_X$ to $C_Y$ olefins comprises reacting at least a portion of a feedstock comprising $C_5$ and $C_6$ olefins under dimerization conditions and providing a dimerization product. The dimerization product is separated into a stream comprising unreacted $C_5$ and $C_6$ paraffins, a stream comprising $C_{10}$ to $C_{X-1}$ olefins, and a stream comprising $C_X$ to $C_Y$ olefins. At least a portion of the stream comprising $C_{10}$ to $C_{X-1}$ olefins is reacted with the feedstock under dimerization conditions and the dimerization product is provided. The stream comprising $C_X$ to $C_Y$ olefins is subjected to (a) an alkylation process with benzene under alkylation conditions to produce an alkylation effluent comprising alkylbenzenes and benzene; (b) a sulfonation process to produce a hydrocarbon sulfonate; or (c) a combination of (a) and (b).

A process for making $C_X$ to $C_Y$ olefins in accordance with a further embodiment comprises separating a reaction product into a stream comprising unreacted $C_5$ and $C_6$ paraffins, a stream comprising $C_{10}$ to $C_{X-1}$ olefins, a stream comprising $C_{Y+}$ olefins, and a stream comprising $C_X$ to $C_Y$ olefins. At least a portion of a feedstock comprising $C_5$ and $C_6$ olefins is reacted under dimerization conditions to provide a first portion of the reaction product. The stream comprising $C_{10}$ to $C_{X-1}$ olefins and the stream comprising $C_{Y+}$ olefins are reacted under metathesis conditions to provide a second portion of the reaction product. The stream comprising $C_X$ to $C_Y$ olefins is subjected to (a) an alkylation process with benzene under alkylation conditions to produce an alkylation effluent comprising alkylbenzenes and benzene; (b) a sulfonation process to produce a hydrocarbon sulfonate; or (c) a combination of (a) and (b).

BRIEF DESCRIPTION OF THE DRAWINGS

The present invention will hereinafter be described in conjunction with the following drawing figures, wherein like numerals denote like elements, and wherein.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Processes for making heavy $C_X$ to $C_Y$ olefins are provided herein. As used herein, "$C_X$ to $C_Y$ olefins" means olefins having a desired or predetermined range of carbons between and including integers X and Y, where X is at least 14 carbons and Y is greater than X and less than or equal to 36. While in a preferred embodiment, the processes contemplated herein produce $C_{18}$ to $C_{28}$ olefins, it will be understood that the methods are not so limited and heavy olefins $C_X$ to $C_Y$ can be produced. As noted above, a typical method for making heavy olefins requires separating heavy olefins from a feedstock also containing heavy paraffins. In contrast, the processes contemplated herein utilize a feedstock containing $C_5$ and $C_6$ paraffins, which is comparably less expensive that heavy paraffins/heavy olefins feedstocks. The processes utilize a $C_{10}$ to $C_{X-1}$ intermediate stream that is circulated through a dimerization and dehydrogenation loop that optimizes the amount of $C_X$ to $C_Y$ mono-olefins produced.

Figure 1:
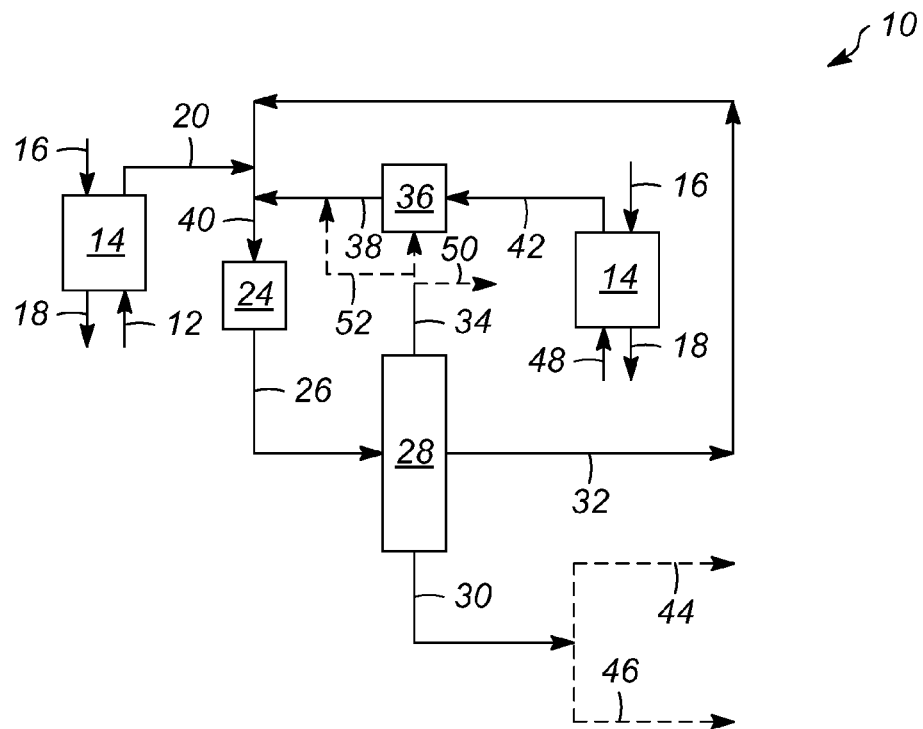
FIG. 1 is a schematic depiction of an apparatus for making heavy olefins in accordance with an exemplary embodiment.

In accordance with an exemplary embodiment, FIG. 1 is a schematic depiction of an apparatus 10 for making $C_X$ to $C_Y$ olefins, preferably $C_{18}$ to $C_{28}$ olefins. In one embodiment, a feedstock 12 containing $C_5$ and $C_6$ paraffins and olefins is provided. One source for such feedstock is from naphtha range fractions from petroleum refining. As branched paraffins and naphthenes are generally preferred for gasoline, normal $C_5$ and $C_6$ paraffins and olefins typically have less value to the refiner. The feedstock may also be obtained from other sources such as, for example, Fischer-Tropsch processes and thus usually contains normal paraffins and olefins. While the feedstocks used in the process embodiments will have different compositions depending upon the source of the feedstocks, the feedstock will nevertheless be predominantly composed of $C_5$ and $C_6$ paraffins. As used herein, a feedstock is predominantly composed of a material when the feedstock contains about 50 mass-percent or more of the material. The olefins generally comprise at least about 1, and preferably about 1 to 50, often between about 10 and 40, and in some cases from about 2 to 10, mass-percent of the feedstock. If the olefins are present in the feedstock in less than this amount, the feedstock preferably is fed to a dehydrogenation reactor before dimerization, as discussed in more detail below. The feedstocks will likely also contain hydrocarbons of higher and lower carbon number. $C_7$ paraffins may be added to the feedstock to increase the molecular weight of the feedstock 12 which in turn will increase the resulting molecular weight of the end products from a dimerization reactor and, if present, a metathesis reactor, to be discussed in more detail below. Typically the feedstocks will have the following compositions:

| Component | Typical, mass-percent | Preferred, mass-percent |
|---|---|---|
| $C_4$ | 0.0 to 10 | 0.0 to 5 |
| $C_5$ and $C_6$ paraffin | 50 to 100 | 60 to 90 |
| $C_5$ and $C_6$ olefins | 1 to 50 | 10 to 40 |
| $C_{7+}$ | 0 to 20 | 0 to 10 |
| Aromatics | 0 to 10 | 0 to 5 |
| Oxygenates | 0 to 3 | 0 to 1 |
| Dienes | 0 to 2 | 0 to 1 |

The feedstock also may comprise oxygenates such as alcohols, aldehydes, ketones, ethers, acids, and esters, and more than one oxygenate may be present, that are to be removed by an oxygenate extractor 14. The extraction is effected using a liquid extractant comprising an alcohol and/or a diol of 1 to 3 carbon atoms per molecule and a minor amount of water under extraction conditions. As used herein, a fluid has a minor amount of a material when the fluid contains about 25 mass-percent or less of the material. The alcohols and diols may be one or more of ethanol, 1-propanol, 2-propanol, ethylene glycol, propylene glycol, 1,3 propanediol, and preferably methanol. The amount of water present in the extractant is usually less than about 25 mass-percent. Although more water can be present, little benefit is normally seen in using the higher concentrations of water. In an exemplary embodiment, a methanol-water sorbent 16 is introduced into extractor 14 and a spent sorbent 18 is withdrawn for regeneration. The spent sorbent 18 will contain in addition to the alcohol or diol water and oxygenates. The alcohol and/or diol can be separated for recycle, for example by stripping or fractionation of the spent sorbent. The oxygenates pass with the water during such separations.

Suitable extraction conditions maintain the extractant and the feedstock in liquid phase during the extraction. In an exemplary embodiment, the extraction is conducted at temperatures in the range of from about 15° C. (59° F.) to 150° C. (302° F.), preferably 30° C. (86° F.) to 120° C. (258° F.), and pressures of from about 100 kPa(a) (14.5 psi(a)) to 5000 kPa(a) (725 psi(a)), preferably from about 150 kPa(a) (21.8 psi(a)) to 1000 kPa(a) (145 psi(a)). The extraction operation may be operated in any convenient manner. The contact time is between about 5 seconds to about 10 minutes or as sufficient to provide the desired reduction in oxygenate content. The extraction may be conducted, for example, in a liquid-liquid column, which, if desired, contains packing to assist in liquid-liquid contact. The extraction can also be effected in a vessel in which the liquid streams are agitated.

The feedstock, with at least a portion of the oxygenates removed, now designated feedstock 20, passes from the oxygenate extractor to a dimerization reactor 24. Within the dimerization reactor 24, the feedstock 20, which contains $C_5$ and $C_6$ paraffins and olefins, is subjected to dimerization conditions sufficient to provide a $C_{10}$ to $C_{X-1}$ mono-olefin product.

Dimerization conditions include the presence of a catalyst and the use of elevated temperatures and pressures. The specific temperature and pressure conditions used will depend, at least in part, upon the type of catalyst employed. Both homogeneous and heterogeneous catalysts can be used. Examples of homogeneous catalysts include hydrogen fluoride, boron trifluoride, and trifluoroacetic acid. Heterogeneous catalysts include suitable silica-aluminas, sulfated zirconias, and molecular sieves and supported metal-containing catalysts that often contain at least one element selected from Groups 3, 4, 8 to 10, and 14 of the Periodic Table. References herein to the Periodic Table are to the new IUPAC notation as shown on the Periodic Table of Elements in the inside front cover of the CRC Handbook of Chemistry and Physics, $80^{th}$ Edition, 1999-2000, CRC Press, Boca Raton, Fla., USA. In an exemplary embodiment, temperatures for the dimerization are in the range of about 40° C. (104° F.) to 250° C. (482° F.), preferably 60° C. (140° F.) to 200° C. (392° F.), and pressures of from about 100 kPa(a) (14.5 psi(a)) to 2000 kPa(a) (290 psi(a)), preferably from about 110 kPa(a) (16 psi(a)) to 1000 kPa(a) (145 psi(a)). The dimerization conditions are controlled to minimize the production of $C_{Y+}$ olefins. Preferably, the dimerization conditions are such that on a per mass basis at least about 20, more preferably about 30 to 70, mass-percent of the olefin is converted to dimers and higher with at least about 70, preferably at least about 75, mass-percent of the conversion being to dimers. Preferably, little, if any, $C_{10}$ to $C_{X-1}$ paraffins are formed during the dimerization, and the dimerization product contains less than about 0.1, preferably less than about 0.01, mass-percent $C_{10}$ to $C_{X-1}$ paraffins.

Heterogeneous dimerization catalyst may be in a fixed bed, a moving catalyst bed, or a fluidized bed. A dimerization zone within the reactor 24 comprises one or more catalyst-containing reaction zones with heat exchangers there between to ensure that the desired reaction temperature is maintained at the entrance to each reaction zone. Preferably more than one reaction zone is used with intervening fractionation to remove dimerized product. Each reaction zone is operated in a continuous or batch-type manner and contains one or more catalyst beds. Hydrocarbons may contact any catalyst bed in an upward-, downward-, or radial-flow fashion.

In another embodiment, dimerization reactor 24 also may serve as an oligomerization reactor. In this regard, dimerization reactor 24 can use the same catalyst as when reactor 24 is performing dimerization but will operate under temperatures, pressures and residence times so as to achieve oligomerization. Temperatures for the oligomerization are generally in the range of about 100° C. (212° F.) to 250° C. (482° F.), preferably 120° C. (248° F.) to 200° C. (392° F.), and pressures of from about 100 kPa(a) (14.5 psi(a)) to 2000 kPa(a) (290 psi(a)), preferably from about 110 kPa(a) (16 psi(a)) to 1000 kPa(a) (145 psi(a)). While dimerization or oligomerization may be the predominant reactions in reactor 24, some metathesis may also occur therein.

A dimerized or oligomerized olefin-containing effluent 26 passes from the dimerization reactor 24 to a fractionation apparatus 28 from which a product stream 30 comprising $C_X$ to $C_Y$ olefins is removed, as is a stream 32 comprising predominantly $C_{10}$ to $C_{X-1}$ mono-olefins, and a stream 34 comprising unreacted $C_5$ and $C_6$ paraffins and olefins. While fractionation apparatus 28 is shown with one fractionation column in FIG. 1, it will be appreciated that fractionation apparatus 28 may comprise more than one fractionation column as is necessary to separate and remove the streams 30, 32, and 34. Upon fractionation, at least a portion of product stream 30 may pass as a stream 44 to an alkylation reactor (not shown) for reaction with benzene to produce alkylbenzene, as is well known in the art. Alternatively, or in addition, at least another portion of product stream 30 may pass as a stream 46 to a sulfonation process (not shown) to produce sulfur-based surfactants. A process for sulfonating olefins is described in EP 0351928, "A Process for the Preparation of Internal Olefin Sulfonates," Stapersma, Jan. 24, 1990. Stream 32 comprising predominantly $C_{10}$ to $C_{X-1}$ mono-olefins passes from the fractionation apparatus 28 and combines with feedstock 20 to form stream 40, which is introduced into the dimerization reactor 24. By recycling stream 32 to the dimerization reactor 24, enhanced efficiency is achieved as the stream 40 to the dimerization reactor 24 contains more olefins and higher molecular weight olefins than feedstock 20 alone.

In one embodiment, stream 34 comprising unreacted $C_5$ and $C_6$ paraffins and olefins is directed to a dehydrogenation reactor 36 to convert at least a portion of the paraffins to olefins. The dehydrogenation is conducted in the presence of hydrogen and dehydrogenation catalyst under dehydrogenation conditions including elevated temperature. Any suitable dehydrogenation system may be used. The dehydrogenation conditions are selected to minimize cracking, polyolefin by-products, and skeletal isomerization of the hydrocarbons. Dehydrogenation conditions include a temperature of about 400° C. (752° F.) to 900° C. (1652° F.), preferably 420° C. (788° F.) to 550° C. (1022° F.), a pressure of from about 1 kPa(g) (0.15 psi(g)) to 1000 kPa(g) (145 psi(g)), and a liquid hourly space velocity (LHSV) of from about 0.1 to about 100 $hr^{-1}$. Liquid hourly space velocity is defined as the volumetric flow rate of liquid per hour divided by the catalyst volume, where the liquid volume and the catalyst volume are in the same volumetric units. Generally for normal paraffins, the lower the molecular weight, the higher the temperature required for comparable conversion. The pressure in the dehydrogenation zone is maintained as low as practicable, usually less than 350 kPa(g) (50.8 psi(g)) to maximize chemical equilibrium advantages.

In an alternative embodiment, stream 34 is divided by, for example, a flow separator, into a purge stream 50 and a bypass stream 52. This embodiment may be useful when stream 34 is particularly high in olefins, in which case it may be cost effective to bypass dehydrogenation reactor 36. Stream 34 may be high in olefins because feedstock 12 is high in olefins and/or because of a partial conversion of paraffins to olefins in dimerization reactor 24. In one embodiment, stream 34 is divided into purge stream 50 and bypass stream 52 when stream 34 comprises less than 95% $C_5$ to $C_6$ paraffins. The amount of stream 34 that is purged as purge stream 50 is based, at least in part, on the conversion rate of paraffins to olefins in dimerization reactor 24, the olefin concentration in feedstock 12, and the desired amount of olefin in stream 34. In a further embodiment, purge stream 50 can be recycled back to feedstock 12 and/or feedstock 20 and/or, as discussed in more detail below, feedstock 48 and/or extracted feedstock 42.

In another alternative embodiment, a portion of stream 34 can be separated as bypass stream 52 while the remaining portion of stream 34 continues to dehydrogenation reactor 36. This embodiment may be useful when stream 34 is particularly high in paraffins, in which case it may be cost effective to utilize dehydrogenation reactor 36 to convert a certain amount of the paraffins in stream 34 to olefins. The amount of stream 34 that is passed to dehydrogenation reactor 36 is based on the conversion rate of paraffins to olefins in dimerization reactor 24, the olefin concentration in feedstock 12, and the desired amount of olefin in stream 34. In a further embodiment, all three streams 34, 50, and 52 may be utilized.

In an optional embodiment, instead of (or in addition to) feedstock 12, a feedstock 48 comprising predominately $C_5$ and $C_6$ paraffins and less than 1 mass-percent $C_5$ and $C_6$ olefins is provided to dehydrogenation reactor 36 to convert the paraffins to olefins. As with feedstock 12, if feedstock 48 contains oxygenated compounds, it can be subjected to an oxygenate extraction in oxygenate extractor 14 forming an extracted feedstock 42 that is passed to dehydrogenation reactor 36. Dehydrogenation conditions in reactor 36 are optimized to maximize the olefins content of a resulting dehydrogenated stream 38 exiting the reactor. By combining dehydrogenated stream 38 containing predominantly olefins with stream 32 containing olefins, enhanced efficiency in dimerization can be realized.

Figure 2:
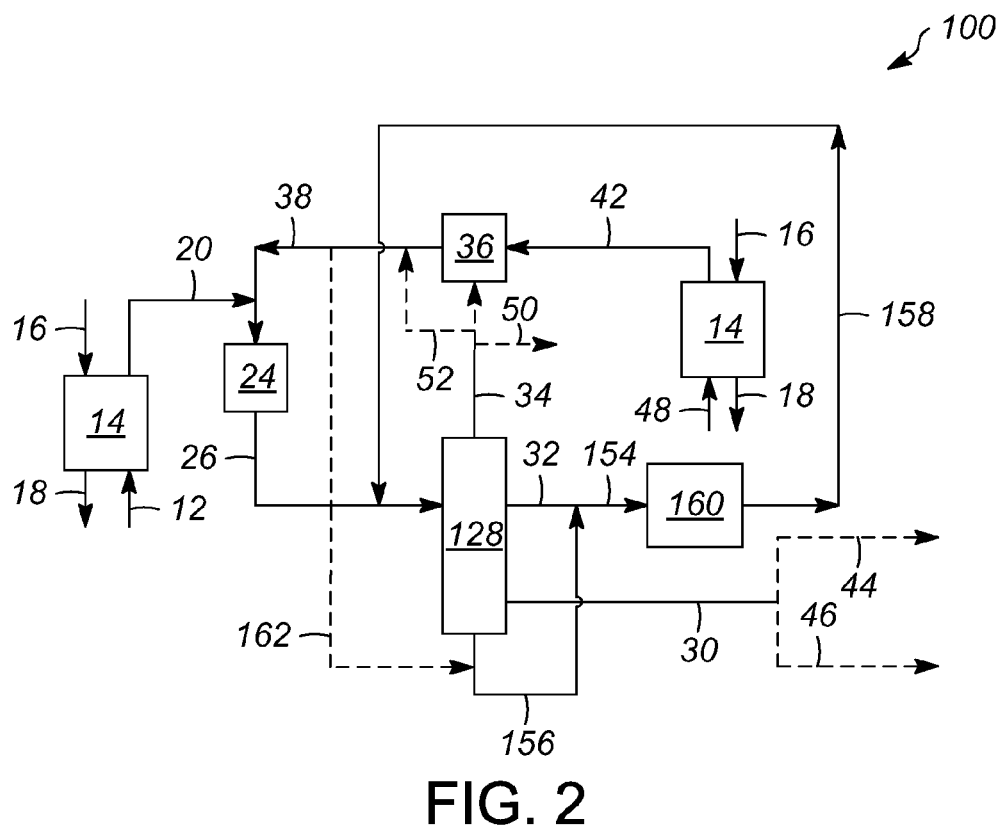
FIG. 2 is a schematic depiction of an apparatus for making heavy olefins in accordance with another exemplary embodiment.

In accordance with another exemplary embodiment, FIG. 2 is a schematic depiction of an apparatus 100 for making $C_X$ to $C_Y$ olefins, preferably $C_{18}$ to $C_{28}$ olefins. Apparatus 100 is similar to apparatus 10 to the extent that apparatus 100 comprises dimerization reactor 24, dehydrogenation reactor 36, and a fractionation apparatus, in this case, fractionation apparatus 128. However, unlike apparatus 10, apparatus 100 comprises a metathesis reactor 160 to react intermediate range olefins ($C_{10}$-$C_{X-1}$) with $C_{Y+}$ olefins to produce heavy olefins ($C_X$-$C_Y$).

In one exemplary embodiment, feedstock 12 containing $C_5$ and $C_6$ paraffins and olefins is provided to oxygenate extractor 14. $C_7$ paraffins may be added to the feedstock to increase the molecular weight of the feedstock 12 which in turn will increase the resulting molecular weight of the end products from the dimerization reactor 24 and metathesis reactor 160, to be discussed in more detail below.

The feedstock 12, with at least a portion of the oxygenates removed, now designated feedstock 20, passes from the oxygenate extractor to dimerization reactor 24. Within the dimerization reactor 24, the feedstock 20, which contains $C_5$ and $C_6$ paraffins and olefins, is subjected to dimerization conditions sufficient to provide a $C_{10}$ to $C_{X-1}$ mono-olefin product. The dimerization conditions within dimerization reactor 24 can be the same conditions as those used with respect to the exemplary embodiments of the processes described with respect to FIG. 1. As with the embodiments of FIG. 1, the dimerization conditions are controlled to minimize the production of $C_{Y+}$ olefins. Preferably, the dimerization conditions are such that on a per mass basis at least about 20, more preferably about 30 to 70, mass-percent of the olefin is converted to dimers and higher with at least about 70, preferably at least about 75, mass-percent of the conversion being to dimers. Preferably, little, if any, $C_{10}$ to $C_{X-1}$ paraffins are formed during the dimerization, and the dimerization product contains less than about 0.1, preferably less than about 0.01, mass-percent $C_{10}$ to $C_{X-1}$ paraffins. In another embodiment, dimerization reactor 24 also may serve as an oligomerization reactor, as described above.

A dimerized or oligomerized olefin-containing effluent 26 passes from the dimerization reactor 24 to a fractionation apparatus 128 where product stream 30 comprising $C_X$ to $C_Y$ olefins is removed, as is stream 32 comprising predominantly $C_{10}$ to $C_{X-1}$ mono-olefins, stream 34 comprising unreacted $C_5$ and C$_6$ paraffins and olefins, and a stream 156 comprising C$_{Y+}$ olefins. While fractionation apparatus 128 is shown with one fractionation column in FIG. 2, it will be appreciated that fractionation apparatus 128 may comprise more than one fractionation column as is necessary to separate the streams 30, 32, 34, and 156. Upon fractionation, at least a portion of product stream 30 may pass as a stream 44 to an alkylation reactor (not shown) for reaction with benzene to produce alkylbenzene. Alternatively, or in addition, at least another portion of product stream 30 may pass as a stream 46 to a sulfonation process (not shown) to produce sulfur-based surfactants. Stream 34 comprising unreacted C$_5$ and C$_6$ paraffins and olefins is directed to dehydrogenation reactor 36 to convert at least a portion of the paraffins to olefins. Alternatively, a portion of stream 34 may be bled off as bypass stream 52 to bypass dehydrogenation reactor 36 and combine with stream 38, stream 34 may be separated into purge stream 50 and bypass stream 52, or the three streams, 34, 50 and 52 may be utilized. The conditions of dehydrogenation reactor 36 can be the same as those used in the exemplary embodiments of the processes described with respect to FIG. 1.

In an optional embodiment, a portion of stream 38, that is, a stream 162, bypasses dimerization reactor 24 and fractionation apparatus 128 to combine with stream 156. While FIG. 2 shows stream 162 combining with 156 before stream 156 combines with stream 32, it will be appreciated that stream 162 can combine with stream 32 before stream 156 combines with stream 32 or can combine with stream 154. By combining stream 162 with stream 156 in this manner, lighter olefins (i.e. C$_5$-C$_6$ olefins) may metathesize easier than heavier olefins and very heavy olefins may combine with light olefins to shorten the carbon chain of the heavy olefins.

Stream 32 comprising predominantly C$_{10}$ to C$_{X-1}$ mono-olefins passes from the fractionation apparatus 128 and combines with stream 156 (with or without stream 162) to form a stream 154, which is introduced into the metathesis reactor 160. By subjecting the heavy olefins (C$_{Y+}$) of stream 156 to metathesis along with C$_{10}$ to C$_{X-1}$ olefins of stream 32, a product stream 158 will comprise substantially olefins in the C$_X$ to C$_Y$ (desired) range, which can be passed directly to the fractionation apparatus 128 for separation as stream 30. While metathesis is the predominant reaction in reactor 160, it will be appreciated that some dimerization and/or oligomerization may also occur.

Metathesis reaction conditions include the presence of a metathesis catalyst. The catalyst may be homogeneous or heterogeneous. Catalytically-active elements proposed for metathesis catalysts include elements from Groups 4, 5, 6, 7, and 8 to 10 of the Periodic Table, including one or more of titanium, niobium, tantalum, molybdenum, tungsten, rhenium, ruthenium, osmium, and iridium, especially one or more of rhenium, tungsten, and molybdenum. The heterogeneous catalysts are generally supported, for instance, on a refractory oxide support or a molecular sieve-containing support. Temperatures for the metathesis are generally in the range of about 20° C. (68° F.) to 300° C. (572° F.), preferably 35° C. (95° F.) to 150° C. (302° F.), and pressures may be within a range of from about 100 kPa(a) (14.5 psi(a)) to 2000 kPa(a) (290 psi(a)), preferably about 110 kPa(a) (16 psi(a)) to 1000 kPa(a) (145 psi(a)).

Heterogeneous metathesis catalysts may be in a fixed bed, a moving catalyst bed, or a fluidized bed. A metathesis zone in the reactor 160 may comprise one or more catalyst-containing reaction zones. Each reaction zone is operated in a continuous or batch-type manner and contains one or more catalyst beds. Hydrocarbons may contact any catalyst bed in an upward-, downward-, or radial-flow fashion. Preferably, the metathesis conditions are such that at least about 30, more preferably about 40 to 95, mass-percent of the olefin is converted to heavy olefins. Preferably, little, if any, C$_X$ to C$_Y$ paraffins are formed during the metathesis, and often the metathesis product contains less than about 0.1, preferably less than about 0.01, mass-percent C$_X$ to C$_Y$ paraffins. The by-products of metathesis are ethylene and propylene that have value, especially in an integrated refinery.

In an optional embodiment, instead of (or in addition to) feedstock 12, feedstock 48 comprising predominately C$_5$ and C$_6$ paraffins and less than 1% mass-percent C$_5$ and C$_6$ olefins is provided to dehydrogenation reactor 36 to convert the paraffins to olefins. As with feedstock 12, if feedstock 48 contains oxygenated compounds, it can be subjected to an oxygenate extraction in oxygenate extractor 14 forming an extracted feedstock 42 that is passed to dehydrogenation reactor 36. Dehydrogenation conditions in reactor 36 are optimized to maximize the olefins content of resulting stream 38 exiting the reactor. By combining dehydrogenated stream 38 containing predominantly olefins with feedstock 20 containing olefins, enhanced efficiency in dimerization can be realized.

Accordingly, processes for making heavy C$_X$ to C$_Y$ olefins have been described herein. The processes contemplated herein utilize a feedstock containing C$_5$ and C$_6$ paraffins, which is comparably less expensive that heavy paraffins/heavy olefins feedstocks. The processes utilize a C$_{10}$ to C$_{X-1}$ intermediate stream that is circulated through a dimerization and dehydrogenation loop that optimizes the amount of C$_X$ to C$_Y$ mono-olefins produced. While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for making C$_X$ to C$_Y$ olefins, the process comprising the steps of:

reacting a feedstock comprising C$_5$ and C$_6$ olefins under dimerization or oligomerization conditions to provide a dimerization or oligomerization product;

separating the dimerization or oligomerization product in a separation unit into a stream comprising unreacted C$_5$ and C$_6$ paraffins, a stream comprising C$_{10}$ to C$_{X-1}$ olefins, a stream comprising CY$_+$ olefins, and a stream comprising C$_X$ to C$_Y$ olefins including olefins having odd numbers of carbons to form a more uniform distribution of olefins, wherein X is at least 14 and Y is greater than X and less than or equal to 36;

reacting a first portion of the stream comprising C$_{10}$ to C$_{X-1}$ olefins under chain growth conditions to provide a portion of the stream comprising C$_X$ to C$_Y$ olefins, wherein the chain growth conditions include dimerization or oligomerization; and reacting at least a portion of the stream comprising C$_{10}$ to C$_{X-1}$ olefins under chain growth conditions to provide the stream comprising C$_X$ to C$_Y$ olefins, wherein chain growth conditions include dimerization or oligomerization;

reacting a second portion of the stream comprising $C_{10}$ to $C_{X-1}$ olefins and the stream comprising $C_{Y+}$ olefins under metathesis conditions to provide a metathesis reaction product and passing the metathesis reaction product to the separation unit.

2. The process of claim 1, wherein the separating step comprises separating the dimerization or oligomerization product into the stream comprising unreacted $C_5$ and $C_6$ paraffins, the stream comprising $C_{10}$ to $C_{X-1}$ olefins, and the stream comprising $C_X$ to $C_Y$ olefins, wherein X is 18 and Y is greater than X and less than or equal to 28.

3. The process of claim 1, wherein the step of reacting the first portion of the stream comprising $C_{10}$ to $C_{X-1}$ olefins comprises reacting at least the portion of the stream comprising $C_{10}$ to $C_{X-1}$ olefins under dimerization conditions.

4. The process of claim 1, further comprising dehydrogenating at least a portion of the stream comprising unreacted $C_5$ and $C_6$ paraffins and recovering a dehydrogenation product comprising $C_5$ and $C_6$ mono-olefins and unreacted $C_5$ and $C_6$ paraffins, and wherein the step of reacting the first portion of the stream comprising $C_{10}$ to $C_{X-1}$ olefins further comprises reacting at least a portion of the dehydrogenation product under chain growth conditions to provide a portion the stream comprising $C_X$ to $C_Y$ olefins.

5. The process of claim 1, further comprising purging a first portion of the unreacted $C_5$ and $C_6$ paraffins and reacting and second portion of the unreacted $C_5$ and $C_6$ paraffins with the feedstock under dimerization or oligomerization conditions.

6. The process of claim 1, further comprising subjecting the stream comprising $C_X$ to $C_Y$ olefins to (a) an alkylation process with benzene under alkylation conditions to produce an alkylation effluent comprising alkylbenzenes and benzene; (b) a sulfonation process to produce a hydrocarbon sulfonate; or (c) a combination of (a) and (b).

7. The process of claim 1, wherein the step of reacting the feedstock comprises reacting the feedstock comprising at least about 1 mass-percent of $C_5$ and $C_6$ olefins.

8. The process of claim 1, further comprising dehydrogenating the feedstock prior to reacting the feedstock.

9. The process of claim 1, further comprising extracting oxygenates from the feedstock prior to reacting the feedstock.

10. A process for making $C_X$ to $C_Y$ olefins, the process comprising the steps of:
    reacting at least a portion of a feedstock comprising $C_5$ and $C_6$ paraffins and olefins in dimerization reactor under dimerization conditions and providing a dimerization product;
    separating the dimerization product in a separation unit into a stream comprising unreacted $C_5$ and $C_6$ paraffins, a stream comprising $C_{10}$ to $C_{X-1}$ olefins, a stream comprising $C_{Y+}$ olefins, and a stream comprising $C_X$ to $C_Y$ olefins including olefins having odd numbers of carbons to form a more uniform distribution of olefins, wherein X is at least 14 and Y is greater than X and less than or equal to 36;
    passing a first portion of the stream comprising $C_{10}$ to $C_{X-1}$ olefins to the dimerization reactor;
    reacting a second portion of the stream comprising $C_{10}$ to $C_{X-1}$ olefins and the stream comprising $C_{Y+}$ olefins under metathesis conditions to provide a metathesis reaction product and passing the metathesis reaction product to the separation unit;
    recycling at least a portion of the stream comprising $C_{10}$ to $C_{X-1}$ olefins to the dimerization reactor; and
    subjecting the stream comprising $C_X$ to $C_Y$ olefins to (a) an alkylation process with benzene under alkylation conditions to produce an alkylation effluent comprising alkylbenzenes and benzene; (b) a sulfonation process to produce a hydrocarbon sulfonate; or (c) a combination of (a) and (b).

11. The process of claim 10, further comprising dehydrogenating the feedstock comprising $C_5$ and $C_6$ paraffins and olefins prior to reacting the feedstock under the dimerization conditions.

12. The process of claim 10, further comprising dehydrogenating at least a portion of the stream comprising unreacted $C_5$ and $C_6$ paraffins and recovering a dehydrogenation product comprising $C_5$ and $C_6$ mono-olefins and unreacted $C_5$ and $C_6$ paraffins, and wherein the step of reacting the first portion of the stream comprising $C_{10}$ to $C_{X-1}$ olefins further comprises reacting at least a portion of the dehydrogenation product with the feedstock under the dimerization conditions and providing a portion of the dimerization product.

13. The process of claim 10, further comprising purging a first portion of the unreacted $C_5$ and $C_6$ paraffins and reacting a second portion of the unreacted $C_5$ and $C_6$ paraffins with the feedstock under the dimerization conditions and providing at least a portion of the dimerization product.

14. The process of claim 10, further comprising dehydrogenating a first portion of the stream comprising unreacted $C_5$ and $C_6$ paraffins and forming a dehydrogenation product and reacting a second portion of the stream comprising unreacted C5 and C6 paraffins with the dehydrogenation product and the feedstock under the dimerization conditions and providing at least a portion of the dimerization product.

15. A process for making $C_X$ to $C_Y$ olefins, the process comprising the steps of:
    reacting at least a portion of a feedstock comprising $C_5$ and $C_6$ olefins and paraffins under dimerization conditions to provide a first reaction product and passing the first reaction product to the separation unit;
    separating the first reaction product in a separation unit into a stream comprising unreacted $C_5$ and $C_6$ paraffins, a stream comprising $C_{10}$ to $C_{X-1}$ olefins, a stream comprising $C_{Y+}$ olefins, and a stream comprising $C_X$ to $C_Y$ olefins including olefins having odd numbers of carbons to form a more uniform distribution of olefins, wherein X is at least 14 and Y is greater than X and less than or equal to 36;
    reacting the stream comprising $C_{10}$ to $C_{X-1}$ olefins and the stream comprising $C_{Y+}$ olefins under metathesis conditions to provide a second reaction product and passing the second reaction product to the separation unit; and
    subjecting the stream comprising $C_X$ to $C_Y$ olefins to (a) an alkylation process with benzene under alkylation conditions to produce an alkylation effluent comprising alkylbenzenes and benzene; (b) a sulfonation process to produce a hydrocarbon sulfonate; or (c) a combination of (a) and (b).

16. The process of claim 15, further comprising dehydrogenating the feedstock comprising $C_5$ and $C_6$ olefins and paraffins prior to reacting the feedstock under the dimerization conditions.

17. The process of claim 15, further comprising dehydrogenating at least a portion of the stream comprising unreacted $C_5$ and $C_6$ paraffins and forming a dehydrogenation product and reacting at least a portion of the dehydrogenation product with the feedstock to form a portion of the first reaction product.

18. The process of claim 15, further comprising purging a first portion of the unreacted $C_5$ and $C_6$ paraffins and reacting a second portion of the unreacted $C_5$ and $C_6$ paraffins with the feedstock under the dimerization conditions and providing at least a portion of the first reaction product.

19. The process of claim 17, further comprising reacting under metathesis conditions a least a portion of the stream comprising unreacted $C_5$ and $C_6$ paraffins separated from the dehydrogenation product or at least a portion of the stream comprising unreacted $C_5$ and $C_6$ paraffins to provide a third reaction product.

* * * * *